United States Patent [19]
Fujino et al.

[11] 3,931,138
[45] Jan. 6, 1976

[54] N-CARBOBENZOXY-PYROGLUTAMYL-HISTIDINE

[75] Inventors: Masahiko Fujino, Hyogo; Shigeru Kobayashi, Osaka; Obayashi, Mikihio, Kyoto; Susumu Shinagawa; Tsunehiko Fukuda, both of Osaka, all of Japan

[73] Assignee: Abbott Laboratories, North Chicago, Ill.

[22] Filed: Sept. 16, 1974

[21] Appl. No.: 506,367

Related U.S. Application Data

[63] Continuation-in-part of Ser. No. 340,893, March 13, 1973, Pat. No. 3,870,694.

[52] U.S. Cl. ..................................... 260/112.5 TR
[51] Int. Cl.² ................... C07C 103/52; C07G 7/00
[58] Field of Search ................................ 260/112.5

[56] References Cited
UNITED STATES PATENTS 3,853,837 12/1974 Fujino et al. ..................... 260/112.5
3,855,198 12/1974 Sarantakis ....................... 260/112.5

OTHER PUBLICATIONS
Gillessen et al., Helv. Chim. Acta, 63–72 (1970).

Primary Examiner—Lewis Gotts
Assistant Examiner—Reginald J. Suyat
Attorney, Agent, or Firm—Paul D. Burgauer; Robert L. Niblack

[57] ABSTRACT

A method for making N-carbobenzoxy-pGlu-His which is an important intermediate for the manufacture of several releasing hormones. The new product is made by a rapid method which produces good yields and good quality dipeptide material.

2 Claims, No Drawings

N-CARBOBENZOXY-PYROGLUTAMYL-HISTIDINE

BACKGROUND OF THE INVENTION

This application is a continuation-in-part of our earlier application Ser. No. 340,893, filed Mar. 13, 1973, now U.S. Pat. No. 3,870,694.

DETAILED DESCRIPTION OF THE INVENTION

N-carbobenzoxy-pyroglutamyl-histidine, hereinafter referred to as Z-pGlu-His is an N-protected dipeptide that represents an important chemical intermediate in the synthesis of some natural releasing hormones and some synthetic analogs thereof. For instance, the thyrotropin releasing hormone TRH can be made from the above intermediate by a simple condensation which produces essentially the theoretical yield of Z-pGlu-His-Pro-NH$_2$ which, in turn, yields TRH quantitatively.

In a general embodiment, the new Z-pGlu-His is prepared by condensing an active ester of Z-pGlu with histidine. A preferred ester of Z-pGlu for this reaction is the N-hydroxy-5-norbornene-2,3-dicarboximide ester, although other esters such as the N-hydroxy-succinimide, the pentachlorophenyl, the trichlorophenyl, the p-nitrophenyl ester and others that are well known in the peptide art may be used.

In order to illustrate the method of preparing and using the new compound, reference is made to the following example which, however, is not intended to limit the invention in any respect.

EXAMPLE

A solution of 24 g. of Z-L-pGlu in 200 ml. tetrahydrofuran (THF) and 200 ml. of dioxane is cooled in an ice bath and 17.8 g. of N-hydroxy-5-norbornene-2,3-dicarboximide (HONBI) and 21 g. of N,N′-dicyclohexylcarbodiimide are added. The mixture is stirred under ice cooling for 20 minutes and subsequently, 40 minutes at room temperature. At that time, the formed dicyclohexylurea is removed by filtration and the filtrate is evaporated to dryness under reduced pressure.

Recrystallization of the formed crystals from ethyl acetate/petroleum benzine produces the pure Z-L-pGlu-ONBI ester in a yield of 36 g. (94% of theory); m.p. 143.5°–144°C.; $[\alpha]_D^{26} = -41.9°$ ($c = 0.2$, ethanol).

L-histidine hydrochloride (3.6 g.) and 2.5 g. anhydrous sodium carbonate are dissolved in 90 ml. of dioxane/water/DMF 5:4:2 under heating; the solution is rapidly cooled and 8.49 g. of Z-L-pGlu-ONBI is added. The mixture is stirred under ice cooling for 30 minutes and 4 hours at room temperature. The solvents are removed by vacuum distillation and 24 ml. of N hydrochloric acid is added to the residue. The resultant solution is then washed twice with ethyl acetate. The aqueous layer is concentrated to about 20 ml. and allowed to cool overnight at about 5°C. The columnar crystals are separated, washed with water and recrystallized from water containing a small amount of methanol yielding 6.67 g. (78% of theory) of pure Z-L-pGlu-L-His; m.p. 146°–147°C. (decompn.); $[\alpha]_D^{21} = -6.4°$ ($c = 1.12$, methanol).

To a solution of 2.15 g. of Z-L-pGlu-L-His in 30 ml. of DMF is added 1.25 g. of L-prolinamide and 1 g. of HONBI and the mixture is cooled to 0°C, at which time 1.1 g. of dicyclohexylcarbodiimide is added. The mixture is stirred at this temperature for 2 hours and then allowed to stand overnight. The dicyclohexylurea is removed by filtration, the filtrate is evaporated under vacuum and the residue is triturated with 30 ml. of ether. The ether is removed, 20 ml. of chloroform is added and the solution is passed over a 60 g. column of silica gel. The column is washed with 300 ml. of methanol/chloroform 1:19 and eluted with a 20% methanol/chloroform solution. Routine recovery of the material from this solution yields 2.4 g. (96% of theory) of Z-L-pGlu-L-His-L-Pro-NH$_2$ as a white powder. From this material, TRH is obtained by catalytic reduction over palladium black in methanol, producing this material in quantitative yield and highest purity; $[\alpha]_D^{23} = -42.0°$ ($c = 1.0$, methanol), $[\alpha]_D^{23} = -43.2°$ ($c = 0.6$, acetic acid).

The new material Z-pGlu-His is an advantageous intermediate for making peptides containing this sequence particularly because it is obtainable in excellent purity, in high yield and in crystalline form. This latter is a totally unexpected characteristic as peptides containing the histidine moiety often are not easily obtained in high purity and not expected to be crystallizable.

We claim:
1. Carbobenzoxy-pyroglutamyl-histidine.
2. The compound of claim 1 wherein both aminoacids are in the L-form.

* * * * *